United States Patent
Oginski et al.

(10) Patent No.: US 9,999,480 B2
(45) Date of Patent: Jun. 19, 2018

(54) MOUNTING DEVICE FOR A STAND DEVICE AND MOUNTING SYSTEM INCLUDING THE MOUNTING DEVICE

(71) Applicant: Ondal Medical Systems GmbH, Hünfeld (DE)

(72) Inventors: Stefan Oginski, Fulda (DE); Markus Höser, Tann (DE); Andreas Göbel, Eiterfeld (DE)

(73) Assignee: Ondal Medical Systems GmbH, Hünfeld (DE)

( * ) Notice: Subject to any disclaimer, the term of this patent is extended or adjusted under 35 U.S.C. 154(b) by 0 days. days.

(21) Appl. No.: 15/517,908

(22) PCT Filed: Oct. 19, 2015

(86) PCT No.: PCT/EP2015/002062
§ 371 (c)(1),
(2) Date: Apr. 7, 2017

(87) PCT Pub. No.: WO2016/058707
PCT Pub. Date: Apr. 21, 2016

(65) Prior Publication Data
US 2017/0304022 A1 Oct. 26, 2017

(30) Foreign Application Priority Data
Oct. 17, 2014 (EP) .................................... 14003556

(51) Int. Cl.
*A47F 5/00* (2006.01)
*A61B 90/50* (2016.01)
(Continued)

(52) U.S. Cl.
CPC .............. *A61B 90/50* (2016.02); *A61B 90/25* (2016.02); *F16M 11/06* (2013.01); *A61G 12/004* (2013.01)

(58) Field of Classification Search
USPC ... 248/276.1, 282.1, 283.1, 289.11, 324, 327
See application file for complete search history.

(56) References Cited

U.S. PATENT DOCUMENTS

| 2,795,859 | A | * | 6/1957 | Buschbach | ............ G01B 5/255 248/188.1 |
|---|---|---|---|---|---|
| 4,673,154 | A | | 6/1987 | Karapita | |

(Continued)

FOREIGN PATENT DOCUMENTS

| DE | 31 00 819 A1 | 7/1982 |
|---|---|---|
| DE | 10 2012 001 197 A1 | 7/2013 |

*Primary Examiner* — Terrell L McKinnon
*Assistant Examiner* — Michael McDuffie
(74) *Attorney, Agent, or Firm* — Seed Intellectual Property Law Group LLP (57) ABSTRACT

A mounting device for a stand device for arrangement in the operating room and to position or displace a medical apparatus in the operating room, in particular by means of a rotational movement, incorporates a mounting apparatus, which extends along an axis of rotation in a longitudinal direction and has a cavity, which in particular is cylindrical and which is oriented in the longitudinal direction, for accommodating a rotatably supportable connection component of the stand device, in particular a spindle; and an adjustment apparatus for arranging the connection component in a position, which can be predefined, in relation to the mounting apparatus; wherein the mounting device forms a rotational coupling for supporting the connection component on the mounting apparatus, which rotational coupling can be adjusted about the axis of rotation. The invention further relates to a mounting system including such a mounting device.

19 Claims, 7 Drawing Sheets

(51) Int. Cl.
*F16M 11/06* (2006.01)
*A61B 90/25* (2016.01)
*A61G 12/00* (2006.01)

(56) References Cited

U.S. PATENT DOCUMENTS

| | | | | |
|---|---|---|---|---|
| 4,687,167 A * | 8/1987 | Skalka | ............... | A47B 21/0314 |
| | | | | 108/103 |
| 4,738,369 A | 4/1988 | Desjardins | | |
| 4,948,083 A * | 8/1990 | McNaney, Jr. | ........ | A01K 91/08 |
| | | | | 248/289.11 |
| 6,095,468 A * | 8/2000 | Chirico | ............. | F16M 11/2014 |
| | | | | 248/125.7 |
| 6,443,596 B1 * | 9/2002 | Bulko | ........................ | F21V 7/09 |
| | | | | 362/293 |
| 6,639,623 B2 * | 10/2003 | Howell | ................... | E04B 9/006 |
| | | | | 348/370 |
| 7,097,145 B2 * | 8/2006 | Turner | .................. | F16M 11/10 |
| | | | | 248/274.1 |
| 7,770,860 B1 * | 8/2010 | Culpepper | ........... | A61G 12/002 |
| | | | | 248/324 |
| 8,197,154 B2 * | 6/2012 | Broering | ................ | F21V 21/28 |
| | | | | 248/274.1 |
| 8,276,867 B2 * | 10/2012 | Hung | .................... | F16M 11/08 |
| | | | | 248/274.1 |
| 8,602,367 B2 * | 12/2013 | Wang | ................... | F16M 11/046 |
| | | | | 211/206 |
| 8,876,075 B2 * | 11/2014 | Diez | .................. | F16M 11/2014 |
| | | | | 248/274.1 |
| 9,022,339 B2 * | 5/2015 | Borg | ........................ | H02G 7/05 |
| | | | | 248/323 |
| 9,239,127 B2 * | 1/2016 | Kronung | ................. | F16C 11/10 |
| 2003/0052245 A1 * | 3/2003 | McKeown | ............... | G05G 5/12 |
| | | | | 248/276.1 |
| 2003/0141426 A1 * | 7/2003 | Wagner | .................. | F16M 11/10 |
| | | | | 248/324 |
| 2003/0173482 A1 * | 9/2003 | Kuhn | .................... | F16M 11/08 |
| | | | | 248/276.1 |
| 2009/0213596 A1 * | 8/2009 | Gull | ....................... | F16M 11/08 |
| | | | | 362/382 |
| 2013/0187022 A1 * | 7/2013 | Duportal | ................ | G01B 5/008 |
| | | | | 248/543 |
| 2015/0316200 A1 * | 11/2015 | Hoshi | ................. | F16M 13/022 |
| | | | | 248/289.11 |

\* cited by examiner

MOUNTING DEVICE FOR A STAND DEVICE AND MOUNTING SYSTEM INCLUDING THE MOUNTING DEVICE

BACKGROUND

Technical Field

The present invention relates to a mounting device for a stand device for arrangement in an operating room and for positioning or displacing a medical device in an operating room, comprising: a mounting apparatus extending along an axis of rotation in a longitudinal direction having a cavity aligned in the longitudinal direction to accommodate a rotatably supportable connection component of the stand device; and an adjustment apparatus for arranging the connection component in a predefined position in relation to the mounting apparatus. In particular, the present invention relates to a mounting device including the single features of claim 1, and a mounting system including single features of the independent system claim.

Description of the Related Art

Stands, in particular ceiling stands, such as for example, ceiling supply units, monitor supports, or so-called spring arms or central axes, usually comprise one or more carriers arranged rigidly or in a way to be adjustable in height regarding a vertical axis, by means of which an attached medical device may be moved and positioned, for example, in an operating room, in particular also in an intensive care unit. Supply units are usually attached to the stands, on which medical devices are arranged, for example, which will be supplied with required media during a surgery, for example. The carriers define a radius of action of the medical device within which the medical device can be positioned. The carriers are usually rotatable around at least one rotatable connection, in particular a rotary joint. The carriers are optionally arranged to be vertically adjustable and/or vertically pivotable around an at least approximately horizontally aligned axis.

Usually the stand is mounted on a ceiling or adjacent to a subceiling of an operating room. Here, the subceiling is used to mount cables, for example, but not to support the stand. Hereto the stand comprises a ceiling tube, for example. Often alignment of the rotational position of the stand relative to the ceiling or to a ceiling flange has to be executed. The rotational position of the stand relative to a mounting point on the ceiling defines the radius of action. For mounting of the stand mounting devices that include disks or flange plates shrink-fitted on the spindle, for example, may be used. The shrink-fitted disks may be screwed radially with the ceiling tube. However, the solution has some drawbacks in design, in particular due to special gap dimensions and component tolerances. The flange plates may be connected with the spindle and the ceiling tube, respectively, but do not allow an easy and exact adjustment in prior art.

It is an object of the present invention to provide a mounting device by means of which an orientation of the spindle and thus a definition of the radius of action of the stand device in the operating room may be defined and adjusted as exactly as possible. The object is to provide a mounting device by means of which an adjustment or readjustment of the radius of action may be performed in a particularly simple way. Preferably, the mounting device has a high degree of bearing capacity and is suited to accommodate and transfer high weights. Preferably, the mounting device has a simple design and can be manufactured inexpensively. Preferably, the mounting device is mountable and adjustable in a simple way.

BRIEF SUMMARY

This object is solved by a mounting apparatus for a stand device for arrangement in an operating room and for positioning or displacing the medical device in the operating room, in particular by a rotational movement, comprising: a mounting apparatus extending along an axis of rotation in a longitudinal direction with a cavity, which in particular is cylindrical and is aligned in the longitudinal direction to accommodate a rotatably supportable connection component of the stand device; and an adjustment apparatus for arranging the connection component in a position which may be predefined in relation to the mounting device; wherein the mounting apparatus forms a rotational coupling that is adjustable around the axis of rotation for supporting the connection component on the mounting apparatus. This way an adjustment or readjustment of the relative rotational position of the spindle in relation to the mounting device is simple. The radius of action of the stand may be defined in a simple way.

Preferably, the rotational coupling may be adjusted without having to disassemble any components of the mounting device or stand device except from a cover or individual removable parts of a cover.

Preferably, in a first state the mounting apparatus is configured to support the connection component in a rotatable and axially fixed manner, and in a second state to support the connection component in a rotatably fixed and axially fixed manner, in particular when coupled with the adjustment apparatus. This enables the adjustment of predefined rotation angle positions by using the adjustment apparatus.

A stand device is preferably a device for holding, arranging and/or fixing a position, and/or displacing of at least one medical device which may be fixedly mounted or arranged on a wall (in a wall bearing), on a room ceiling, or also on a floor of an operating room, or any other room, so, for example, a ceiling stand, for medical purposes. Thus, the stand device may not have a completely unrestricted movement in the operating room, but may only be movable within a certain radius of action, in particular, relative to a fastening point or mounting point on a room ceiling or wall of the operating room. The stand device may be formed as a ceiling supply unit mounted on a ceiling, and include one or more supply units that are supported on one or two carrier arms and are positionable. The stand device may also be adapted as a monitor support. The stand device may also be adapted as a so-called spring arm, in particular one that is mounted on a wall and includes a light, for example. The stand device may also be adapted as a so-called central axis, in particular, mounted on a ceiling and comprising a plurality of carrier systems, each having at least one carrier, on which a monitor or a light is attached, for example. The stand device preferably has at least two support arms.

A medical device is preferably a supply unit by means of which the means for treating a patient and/or instruments for a surgeon and/or light, clean air, or other media required in the operating room can be provided. The medical device preferably includes some kind of control panel and/or some kind of display device, for graphically displaying patient data, for example.

Here the mounting apparatus is preferably a device by means of which a stand device may be mounted on a room ceiling and which forms a coupling in connection with a connection component of the stand device, in particular a rotational coupling with a spindle. The mounting apparatus may comprise a ceiling flange or may be mounted on a ceiling flange by one or more supports.

A connection component is preferably a component by means of which single carriers of the stand device may be connected to the mounting device and preferably also to one another. At a stand device adapted as a so-called central axis, the connection component may be adapted as centrally arranged spindle which supports several carriers or carrier arms.

An adjustment apparatus preferably is a device by means of which the connection component may be aligned to or adjusted in a determined relative position in relation to the mounting apparatus. By using an adjustment apparatus, individual relative positions may be predetermined. The adjustment apparatus is preferably supported on the connection component in a rotationally fixed manner. According to a variant, the adjustment apparatus functions only as a rotational lock, but not as an axial lock.

Preferably, a rotational coupling is a connection by means of which a coupling may be ensured in a predetermined rotational position, wherein relative rotational movement is possible either in steps or continuously.

An operating room may also be an examination room or an intensive care unit, or a room for performing medical treatments or therapies.

According to an exemplary embodiment the adjustable rotational coupling is formed by the adjustment apparatus and the mounting apparatus, wherein the adjustment apparatus is mountable in a predetermined rotational position about the axis of rotation in relation to the mounting device and is supportable in a rotationally fixed manner. This way an adjustment may be performed by rotating the adjustment apparatus in relation to the mounting apparatus. Here the adjustment apparatus is configured to support the connection component in a rotationally locked manner on the mounting apparatus.

According to a variant the adjustment apparatus is formed as an individual component of the mounting device separate from the connection component and separate from the mounting apparatus. By configuring the adjustment apparatus as an individual unit separate from the spindle a coupling may be provided by means of which the position of the spindle may be adjusted in relation to the mounting apparatus in a flexible and simple way. Preferably the mounting device is coupled to the connection component in a formfitting manner, particularly in different axial positions. This kind terface enables the arrangement of different numbers of carriers or carriers with different dimensions without having to change the interface design, for example.

Optionally the adjustment apparatus may form an integral component in connection with the connection component. For example, the adjustment apparatus may be connected materially with the connection component, in particular welded to it.

The cavity is formed geometrically corresponding to the connection component and provides a rotary bearing to the connection component. This way the connection component in the mounting apparatus may be rotated in order to adjust the rotational position.

Preferably, the mounting apparatus and the adjustment apparatus are arranged axially in series to one another and overlap the connection component, respectively.

According to an exemplary embodiment the adjustment apparatus includes a rotational stop, in particular a groove or spring, which is formed to correspond geometrically to a rotational stop, in particular groove or spring, arranged at the connection component. This way a rotation of the adjustment apparatus may cause a rotation of the spindle and vice versa. Thus, defining the rotational position of the adjustment apparatus relative to the mounting apparatus also enables adjustment of the rotational position of the spindle in the operating room directly. Preferably, the groove extends at least approximately in a longitudinal direction. The rotational lock may optionally be formed as a formfitting coupling, for example a sprocket, any steps or crosspieces that radially engage with one another. The rotational lock may also be used for centering.

Preferably, the mounting apparatus is configured to provide a lock against rotation, in particular by using an axially arranged passage, and also to provide a lock of the connection component in the axial direction, in particular by means of at least one radially arranged passage. This way the readjusting or adjusting of the rotational coupling may be performed smoothly without the need for any other tools or support devices, even if the stand device has significant own mass, for example in cases where a complete supply unit is fastened to the stand device.

According to an exemplary embodiment the adjustment apparatus comprises a plurality of coupling points, in particular openings or passages, to define one of a plurality of rotational positions of the rotational coupling, respectively, which are preferably arranged on a pitch circle, wherein the adjustment apparatus preferably has an annular geometry or is adapted as an annular disk (flat ring). Each of the coupling points is accessible preferably via the upper side of the adjustment apparatus. Preferably, the pitch circle is larger than a diameter of the cavity ensuring good access from the outside. Preferably, the coupling points are arranged on the adjustment apparatus as far as possible radially outwards. This way an adjustment is easy, even in case when an adjustment apparatus is arranged under a ceiling being difficult to access. Preferably, the coupling points are accessible via a front face of the adjustment apparatus. Preferably, the openings or passages are aligned axially, in particular parallel to the axis of rotation.

The adjustment apparatus preferably includes an outer diameter that is larger than or equal to further components of the mounting device. This way the mounting apparatus may provide an interface at a peripheral surface or an outer edge, in particular mounting slots, to which a cover or enclosure of the mounting device may be mounted. Fastening a cover to the adjustment apparatus provides the advantage that the cover is easy to remove and that access to the rotational coupling is simple.

The adjustment apparatus may comprise an annular support surface that is formed to correspond geometrically to an annular support surface of the connection component. Thus, the connection component can be exactly coupled to the adjustment apparatus. The support surface may thus act as a stop for a corresponding step of the connection component.

According to a variant, the adjustment apparatus includes a passage with an inner diameter smaller than the diameter of the cavity or smaller than the inner diameter of an inner lateral surface of the mounting apparatus. This way the connection component may abut on a step of the connection component on the adjustment apparatus.

According to an exemplary embodiment the mounting apparatus comprises a planar lower front face onto which the adjustment apparatus may abut in a predefined axial position. This way the adjustment apparatus may be exactly aligned in relation to the mounting apparatus, thus allowing a rotational lock element to be arranged in different positions, in particular manually, without jamming.

According to an exemplary embodiment the mounting apparatus comprises at least one fastening portion with a plurality of fastening means, in particular openings or bores, wherein the fastening means define the different axial mounting positions. This way a particular vertical position of the stand device in relation to a ceiling or ceiling flange may be adjusted in a simple way.

Preferably, the mounting apparatus comprises 15 to 30, preferably 20 to 25 openings, thus a relative rotational position of the spindle relative to the mounting apparatus may be adjusted in comparatively small angular steps, for example in steps of 15°. Such adjustments of the relative rotational position are particularly advantageous regarding stops limiting rotational movements or regarding rotational locks of the stand device. Thus, the radius of action of the stand device may be flexibly adjusted to position the medical device.

According to a variant the mounting apparatus comprises a plurality of threaded bores to accommodate fastening elements that can be arranged in a longitudinal direction, wherein the threaded bores are arranged on the same pitch circle as corresponding coupling points/openings of the adjustment apparatus. The threaded bores are preferably arranged on a lower front face of the mounting apparatus and extend at least approximately in the longitudinal direction. This enables a simple mounting and a simple readjustment. Preferably, 3 to 5 threaded bores are provided that are accessible from a lower side in the mounted state of the mounting apparatus, thus, the fastening elements may be plugged-in and fastened, in particular screwed, from below in an axial longitudinal direction. A technician may thus mount any fastening elements below the mounting apparatus, basically without having to his/her change position. Screwing in the radial direction is not required. This also enables the technician to work from a lower height, making the mounting procedure less dangerous by reducing the risk of a fall by the technician, for example. In addition, a visual examination of the fastening elements to ensure that they are in the correct position may be performed easily. Thus a pressure or force that may be applied manually in the mounting direction, that is in the longitudinal direction, may more easily applied exactly in the longitudinal direction.

According to an exemplary embodiment the at least one fastening portion is formed on an outer lateral surface by a crosspiece protruding in the radial direction, wherein the mounting apparatus preferably comprises at least three fastening portions that are arranged in a star shape, in particular spaced equally to one another in a peripheral direction. This way a load (in particular a weight or torque) may be transferred to a force engagement point lying further outwards. In particular, with several fastening portions being symmetrically distributed around the circumference of the mounting apparatus, a force may be transferred to advantageous force engagement points in an uniform way. Also, in the case in which the adjustment apparatus has to be fastened to the mounting apparatus, a predefined rotational position may be set in a comparatively exact manner or in especially small rotational steps or rotation angles, in particular, independent of the diameter of the spindle and largely independent of the loads to be transferred.

Preferably the fastening portions are circumferentially arranged on the outer lateral surface, in particular, spaced uniformly in the peripheral direction. This facilitates adjustments regarding a plurality of different rotation angle positions.

According to an exemplary embodiment the mounting apparatus includes a retainer, in particular tube-shaped/tube-like, for a rotational lock element, wherein the retainer is arranged at an outer side, in particular an outer lateral surface, of the mounting apparatus or constitutes the outer lateral surface at least in sections. This allows for removal or insertion of a rotational lock element in a simple way. Preferably, the retainer comprises a through bore that extends down to the lower front face of the mounting apparatus. A retainer configured in such a way may also be denoted as a locking tube.

Preferably, the retainer is formed to arrange a rotational lock element aligned in the axial direction, in particular a bolt connection in the axial direction. The retainer preferably comprises a lower (in particular tube-like) retainer portion with an axial extension smaller than the length of the rotational lock element.

According to an exemplary embodiment the retainer comprises an access, in particular an access radially from outside, wherein the access is preferably formed as cutout. This facilitates a manual adjustment. Preferably, the access comprises an extension in the axial direction that is larger than a length of a rotational lock element and larger than an axial extension of a lower retainer portion.

The access preferably comprises an upper access region on which a rotational lock element may abut, in particular in a predefined axial position. On the upper access region, a bolt including a rim/head/step may be supported in a way that the rotational coupling may be easily adjusted manually. The bolt may be plugged into the retainer and may only be secured by gravitational force. This way a technician has only to perform a plug-in movement, which is done in very short time. A rotational movement or screwing is not required. This is especially advantageous for positions directly underneath a ceiling that are difficult to access. The rotational lock element may be removed manually and mounted again in a simple way, in particular without using tools. This provides advantages, last but not least, as a technician has both hands free, especially for hard to access mounting points of the stand device. According to a variant the rotational lock element may not only be locked by gravity/gravitational force, but alternatively or in addition by a spring connector.

According to an exemplary embodiment the mounting device comprises an axial lock by means of which the connection component may be supported on the mounting apparatus in a predefined axial position, in particular rotatable in relation to the mounting apparatus. The axial lock may facilitate mounting or also readjustment. The stand may be locked using an axial lock, in particular during the alignment in the rotational position, or during the fixing of individual fastening elements. The mounting device may also reduce the risk of jamming within the mounting apparatus. By using only three main components, the mounting device may thus provide an easily adjustable rotational coupling. Here the coupling consists of three main components, that is the mounting apparatus, the adjustment apparatus or the flat ring, and the axial lock. Here the axial lock may be mounted or remain mounted permanently.

Preferably, the axial lock forms an axially fixed rotary bearing for the connection component together with the cavity, that is, a bearing enabling a rotation in a predefined axial position. The axially fixed rotary bearing provides a degree of freedom of movement around the axis of rotation and prevents a movement along the axis of rotation. According to a variant the axial lock is configured to be mounted permanently and to ensure an axial lock of the connection component in different or any mounting situations.

According to an exemplary embodiment the mounting apparatus is configured to fasten and rotatably support the connection component in a predefined relative axial position, wherein a chamfer, edge or milled recess is provided at an inner lateral surface of the mounting apparatus surrounding the cavity. This way an axially fixed rotary bearing may be formed by simple design components that may be easily mounted during mounting of the stand device. Here, the inner lateral surface of the mounting apparatus may be cylindrical, at least in sections. Preferably, the inner lateral surface comprises one or more chamfers or steps which are configured to center a spindle within the mounting apparatus and to position it in a predefined axial position. For a predefined axial position, the mounting may be performed more or less "blind", which is advantageous for ceiling stands that are difficult to access. This kind of chamfers or steps may also facilitate mounting, in particular on a comparatively soft mounting apparatus (e.g., made from an aluminium material), wherein a comparatively hard spindle (e.g., made from a stainless steel material) is supported. These kind of chamfers or steps may prevent a jamming or the creation of ridges, for example. Preferably the chamfers or steps are arranged in a peripheral direction, in particular continuously.

The chamfers or steps are oriented in an axial direction, preferably spaced in quite large distances from each other, in particular, depending on their respective number, and in particular equidistantly along the mounting apparatus. In such a configuration the inner lateral surface may also be adapted as a plurality of centering surface portions. Preferably, geometrically corresponding chamfers or steps are formed on the spindle. One or more centering surface portions allow a more unrestricted selection of a suitable material for the spindle and/or the mounting apparatus.

According to a variant the mounting may also be simplified by using fitting diameters in different sizes.

According to an exemplary embodiment the axial lock comprises a passage arranged tangentially on the mounting apparatus that passes through an outer lateral surface of the mounting apparatus, preferably at two points, and that intersects an/the inner lateral surface of the mounting apparatus. The passage (in particular a bore or cutout) may be arranged like a secant in relation to the outer lateral surface of the mounting apparatus. In the passage a securing element (in particular a bolt or latch) may be inserted tangentially to the connection component, which may engage with the groove of the connection component and secure the connection component axially in the mounting apparatus. Preferably, the mounting apparatus may be arranged tangentially to the mounting apparatus and formed to correspond geometrically to the passage, in particular at a lower contact face, and this can ensure a solid support. For a tangential latch, a specific geometry having one or more steps may be provided, and for a tangential bolt, the design may be simple, in particular resulting in low costs.

The tangentially aligned passage may intersect an inner lateral surface of the cavity in a way that the latch is arranged further inwards than the inner lateral surface. For example, the latch protrudes about half of its diameter further inwards than the inner lateral surface. A passage arranged as secant has the advantage of providing a comparatively long portion of the latch engagement with the connection component as compared to a radially oriented securing bolt. Thus, the latch is arranged tangentially to the connection component, and engages with a peripheral side of the connection component tangentially in sections on the connection component. In addition, this kind of axial lock has the advantage that the axial lock does not need not to be removed, in particular, when rotating the connection component during mounting. Here friction can be kept relatively low during a relative rotation of the connection component within the cavity. Turning may be performed in a simple way, even for long carrier arms or high torques, in particular by engaging with a recess on the lower side of the adjustment apparatus. The axial lock or the tangential latch may remain in the tangential position.

According to a variant, spacers may be provided between the adjustment apparatus and the lower front face of the mounting apparatus to allow an adjustment of the vertical position of the connection component in relation to the mounting apparatus. In addition, a plurality of tangential passages may be provided one above another in the mounting apparatus, respectively, to accommodate a securing element for an axial lock. Thus, a vertical movement may be performed easily without having to use spacers.

Preferably, a support surface is formed on the passage that is configured to transfer a (weight) force applied from the connection component to the mounting apparatus. According to a variant, the support surface is U-shaped. This way the passages may be manufactured in a cost-efficient way, in particular by milling. Furthermore, notch stresses may be reduced to a minimum in the mounting apparatus and also in the connection component. Preferably, the radius of the passage on the upper side is smaller than the radius on the lower side. This allows for specification of how the respective locking element has to be arranged in the passage. A risk of faulty mounting may thus be reduced.

According to an exemplary embodiment the axial lock comprises at least one securing element, in particular a latch or bolt that is adapted and configured to transfer the weight of the stand device from the connection component to the mounting apparatus. Thus, the rotational position may be readjusted without having to disassemble any components of the stand device, in particular any components of the central axis. During the adjustment of the rotational position, the complete stand device may be supported on the axial lock. In other words, the axial lock is configured to form a rotary bearing for the stand device. This facilitates readjustment significantly due to the fact that only the adjustment apparatus has to be disassembled and then fastened in the readjusted rotational position.

According to an exemplary embodiment the passage and the retainer for the rotational lock element are arranged on the same peripheral surface portion of the mounting apparatus, in particular in a way to be manually accessible from the same side. This facilitates the adjustment and mounting of the device. Thus, the rotational lock element and the securing element for the axial lock may be provided by using spring connectors, namely from the same side or on the same peripheral surface portion. Finally, this is advantageous for mounting.

According to an exemplary embodiment the mounting apparatus is a tube-like casting part, in particular made from aluminium, wherein the mounting apparatus is preferably of one piece. This configuration enables a high stability on the one hand, and a cost-efficient production on the other hand. Here the axial extension around the axis of rotation may be determined at most arbitrarily, depending on the operating conditions and the mounting position. Preferably, a support to connect the mounting apparatus with the ceiling flange is formed as a continuous cast part.

According to a variant no supports are provided. The mounting apparatus preferably comprises threaded channels, in particular at the edge, by means of which the mounting apparatus may be mounted directly on the/a flange plate. Thus, a very cost efficient variant may be provided. The number of components or parts is reduced. The mounting may further be simplified, in particular in applications that require no particularly high flexibility regarding a vertical adjustment.

According to an exemplary embodiment the mounting apparatus includes two mating faces in different sizes which are formed to correspond to the mating faces of the connection component and are configured to facilitate the mounting and to enable a two-point support of the connection component. This is advantageous for secure assembly and a stressable mounting.

According to an exemplary embodiment the adjustment apparatus comprises a plurality of openings to define a rotational position, respectively, that are arranged on a pitch circle in which the adjustment apparatus is annular, wherein the mounting apparatus comprises a tube-like retainer for a rotational lock element, wherein the retainer is arranged at an outer lateral surface of the mounting apparatus, wherein the retainer includes an access radially from outside, wherein the access comprises an upper access region onto which a rotational lock element may abut, wherein the adjustment apparatus comprises a groove or spring that is formed to correspond geometrically to a rotational stop arranged at the connection component, wherein the mounting apparatus comprises an axial lock that comprises a chamfer, edge, or milled recess that is provided on an inner lateral surface of the mounting apparatus surrounding the cavity, wherein the axial lock comprises a passage that is tangentially arranged on the mounting apparatus that passes through an outer lateral surface of the mounting apparatus and intersects an inner lateral surface of the mounting apparatus. Using this configuration a plurality of the advantages of the present invention may be realized.

Advantageously the adjustment apparatus is formed as a flat ring and has an at least 12-point rotational symmetric design regarding the arrangement of the coupling points or openings, in particular an at least 24-point rotational symmetric design. This is, related to the center thereof, the adjacent coupling points or openings are arranged in an angular distance of maximum 30° from one another in an at least 12-point rotational symmetric design and related to the center thereof, the adjacent coupling points or openings are arranged in an angular distance of maximum 15° to one another in an at least 24-point rotational symmetric design.

The object described above is achieved by a mounting system with a mounting device according to the invention, wherein the mounting system comprises the connection component adapted as a spindle and a rotational lock element and at least one securing element as axial lock, wherein the spindle is provided with a peripheral groove or a peripheral step that is formed to correspond geometrically to the securing element. In other words, the mounting system comprises different securing elements for axial locking and rotational locking, respectively. Preferably, both types of securing elements are mountable on the same peripheral position of the mounting apparatus. Here a single securing element may be provided as axial lock. Preferably, two securing elements are provided as an axial lock. Optionally, also three securing elements may be provided as an axial lock.

Preferably, the groove is provided circumferentially and extends orthogonal to a longitudinal direction. A circumferential groove provides the advantage that the bolt of the axial lock may engage with the spindle independent of the respective rotational position. In addition, the spindle may be rotated relative to the mounting apparatus in a simple way, even in cases of a load acting on the axial lock in the axial direction. This facilitates the readjustment or changing of the rotational position.

Preferably, the groove is spaced apart from the front face or a front face stop of the spindle, which corresponds to a distance of the bore to a counter-stop in the cavity when seen in the longitudinal direction. This facilitates mounting, in particular as a front face of the spindle may abut on a/the counter-stop of the mounting apparatus in such a way that the spindle is arranged in the correct axial position to provide an axial lock. In this axial position the bolt may engage tangentially with an outer lateral surface of the spindle. It is not necessary to readjust the axial position. The counter-stop of the mounting apparatus may also be provided as bottom of the cavity or a peripheral annular or disk-shaped counter-stop at the bottom of the cavity.

According to a variant, a step is formed on the spindle that overlaps the adjustment apparatus in a radial direction (in a mounted state). This enables a support of the spindle by means of the adjustment apparatus. Said step may enable the fixation of the adjustment apparatus together with one or more carrier arms by using a lower shaft nut securing the carrier arms. In particular, the mounting may be facilitated by the fact that the adjustment apparatus is secured before inserting the spindle in the mounting apparatus, in particular in the case of a slipping downwards.

As a first mounting step, the mounting apparatus may be mounted on the room ceiling. Then the spindle may be plugged into the cavity of the mounting apparatus from below. Preferably, the adjustment apparatus is already arranged on the spindle and may be fastened to the mounting apparatus. This way the spindle may be positioned on the mounting apparatus in the axial direction. Optionally the spindle may also be secured by an axial lock on the mounting apparatus before it is fastened to the adjustment apparatus, thus the adjustment apparatus may be positioned in a predetermined rotational position without having to accommodate a weight of the spindle via the adjustment apparatus at the same time. This facilitates mounting or later adjustment of a predetermined rotational position.

According to a variant, an outer diameter of the step of the spindle is larger than an inner diameter of a passage of the adjustment apparatus. In this configuration the spindle is optionally mountable by using the adjustment apparatus in an axial direction. The radial overlapping is preferably at least 1 mm.

According to a variant, a rotational stop is arranged below the step, in particular an (adjusting) spring, that is preferably aligned in the longitudinal direction. The rotational stop is formed to correspond geometrically to a rotational stop of the adjustment apparatus. The rotational stop, for example, may be an adjusting spring attached in a corresponding groove of the spindle, or a moulded spring.

According to an exemplary embodiment the mounting system comprises a rotational lock element adapted as bolt engaged in the axial direction and one or two securing elements adapted as latches engaged tangentially, wherein the bolt and latch are arranged adjacent to an access provided in a retainer for the rotational lock element. Said arrangement facilitates adjusting and mounting. Optionally, the tangential latch may also be adapted as bolt.

The object described above is also achieved by an adjustment apparatus for a stand device arrangeable in an operating room to position or displace a medical device, in particular by a rotational movement, wherein the adjustment apparatus is arrangeable at a predetermined rotational angle position on a connection component of the stand device, wherein the adjustment apparatus is configured to comprise a plurality of coupling points, in particular openings or passages to define the rotational position, respectively, wherein the adjustment apparatus is adapted as an annular disk. This results in the previously explained advantages.

The object described above is also achieved by a mounting apparatus for a stand device arrangeable in an operating room to position or displace a medical device, in particular by a rotational movement, wherein the mounting apparatus extends in a longitudinal direction along an axis of rotation, and comprises a cavity, which is in particular cylindrical and is oriented in the longitudinal direction, for accommodating a rotatably supportable connection component of the stand device; wherein the mounting apparatus includes a retainer accessible from outside for a rotational lock element to define a rotational position, wherein the mounting apparatus is configured to transfer a torque between the connection component and a flange plate by means of the rotational lock element. This results in the previously explained advantages.

The object described above is also achieved by using an adjustment apparatus according to the invention and/or a mounting apparatus according to the invention, respectively, on a stand device arranged in an operating room to position or displace a medical device, in particular by a rotational movement, wherein the adjustment apparatus and/or the mounting apparatus define an adjustable rotational position of a connection component of the stand device in relation to a flange plate by means of which the stand device is fastened in the operating room. This results in the previously explained advantages.

BRIEF DESCRIPTION OF THE SEVERAL VIEWS OF THE DRAWINGS

The invention will be explained in greater detail in the following figures with the help of exemplary embodiments. Illustrated are.

When describing the following figures, for reference numbers that are not explicitly explained in a figure, reference is made to the other figures.

DETAILED DESCRIPTION

Figure 1:
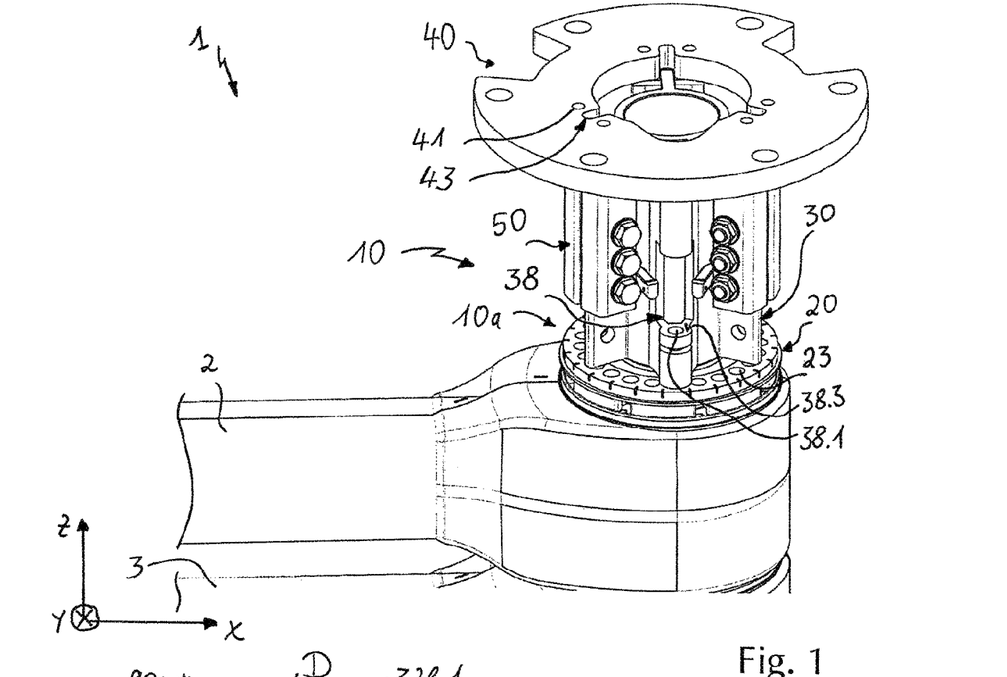
In FIG. 1 in a perspective side view a mounting device according to an exemplary embodiment of the invention in an arrangement mounted to a stand device.

In FIG. 1 a stand device for mounting on a ceiling is shown. The stand device 1 comprises a first carrier 2 and a second carrier 3 which are rotatably supported in a rotary bearing above one another about an axis of rotation. In order to mount the stand device 1 on an (sub)ceiling two carriers 2, 3 are connected or coupled indirectly to a mounting device 10, which comprises an adaptable mechanism 10a adapted as an adjustable rotational coupling. The stand device 1 may be mounted by using a flange plate 40 to a ceiling or subceiling. The flange plate 40 comprises openings 41, in particular bores, through which fastening means, for example screws, may be mounted. Mounting is performed by means of supports 50 ensuring a connection of the flange plate 40 to a mounting apparatus 30. The mounting apparatus 30 works together with an adjustment apparatus 20. The adjustment apparatus 20 may also be denoted as a flat ring. Hereto, the mounting apparatus 30 comprises a rotational lock, in particular a retainer 38 adapted as a tube-like portion, to accommodate a securing element. On an upper access region 38.3 a bolt or pin may be inserted through the through bore 38.1 which works together with a specific coupling point 23 of the adjustment apparatus. Here, a plurality of coupling points 23 define a specific rotational position, respectively. The coupling points 23 may be configured as openings or bores or slots or recesses that are open on the side, for example.

Here a coordinate system designates a horizontal and when mounted to the ceiling also a radial x direction and a vertical z direction.

The adjustment apparatus 20 may thus be supported on an inner ring of a ball bearing arranged in carrier 2 on carrier 2.

Figure 2:
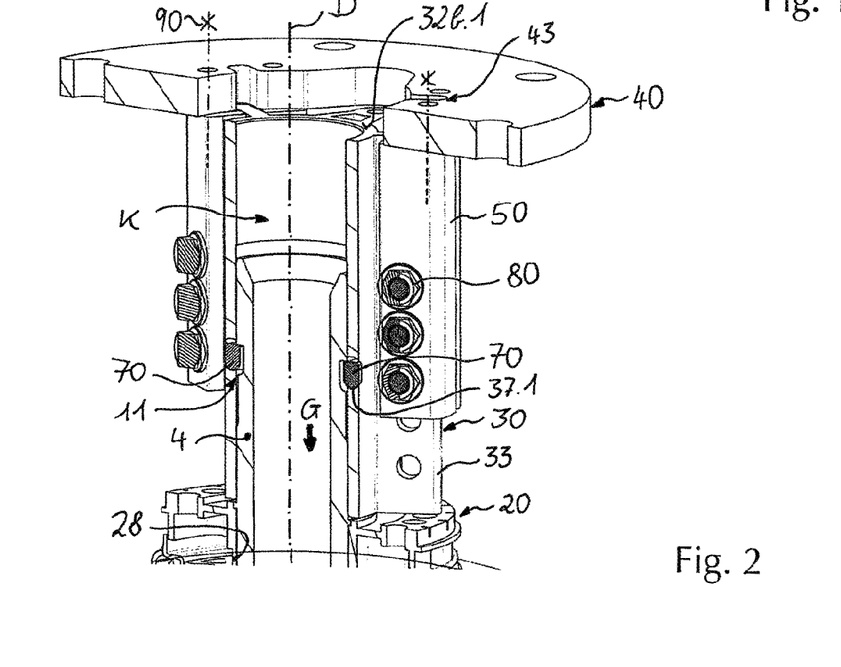
In FIG. 2 a perspective side view of the mounting device shown in FIG. 1.

FIG. 2 shows how the flange plate 40 is connected to the mounting apparatus 30. The flange plate 40 comprises several radial grooves 43 that are adapted to correspond geometrically to the fastening portions 33 of the mounting apparatus 30. Here the flange plate 40 may be fastened to the supports 50 by using fastening elements 90, in particular screws, in a way that a weight G of the connection component 4, in particular a spindle, supported on the mounting apparatus 30 may be transferred via the mounting apparatus 30, the supports 50, and the fastening elements 90 to the flange plate 40 and thus to a ceiling or subceiling. The spindle 4 is supported in the cavity K formed by the mounting apparatus 30. Thus, a relative rotation of the spindle 4 in relation to the mounting apparatus 30 may be performed. The arrangement shown is thus rotatably supported about an axis of rotation D in z direction. The relative rotatability can be prevented by means of the adjustment apparatus 20.

An relative axial movement or displacement downwards is prevented by providing an axial lock 11, onto which the spindle 4 abuts. In the example shown, the axial lock 11 is formed by a plurality of securing elements 17, in particular latches or bolts, which are arranged tangentially to an axis of rotation D and which engage with the spindle 4 and also with the mounting apparatus 30.

A mounting apparatus 30 may be mounted in different relative axial positions (vertical positions) relative to the supports 50 or to the flange plate 40, namely by means of fastening elements 80, in particular screws, which engage with corresponding openings or through bores at the respective fastening portion 33 or at the respective support 50.

Figure 3:
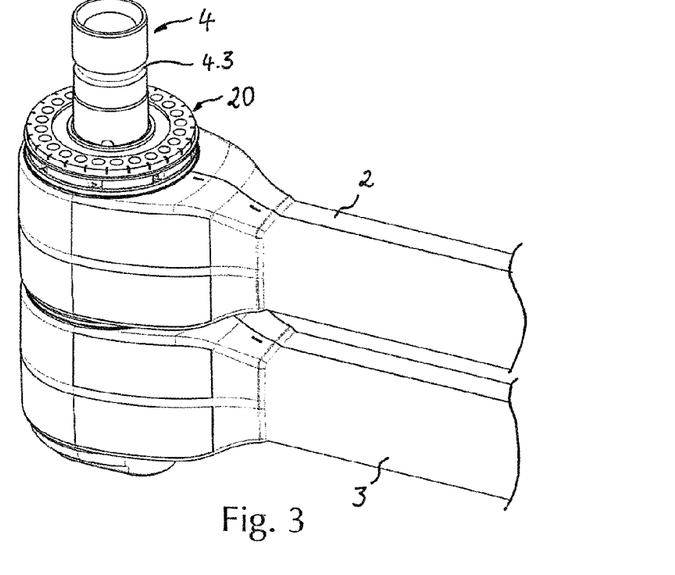
In FIG. 3 a perspective side view from above of an adjustment apparatus of the mounting device shown in FIG. 1, wherein the adjustment apparatus is arranged around a spindle of the stand device.

FIG. 3 shows how the spindle 4 is inserted in the cavity K of the mounting apparatus 30 from below. Thus the securing elements 70 described above may cooperate with the peripheral groove 4.3 in the end position. Here, the spindle 4 is rotatably supported on the groove 4.3 and supported in the cavity K in an axially fixed way.

Figure 4:
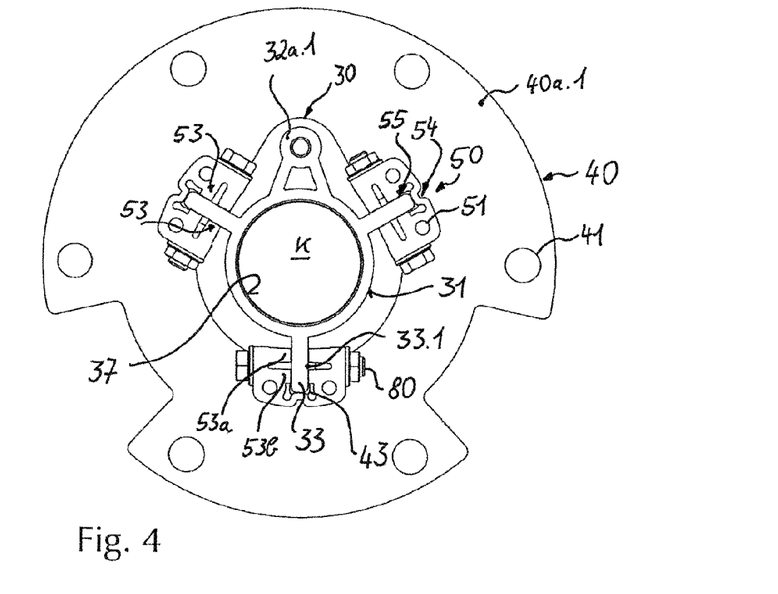
In FIG. 4 in plan view from below individual components of the mounting device shown in FIG. 1.
Figure 5:
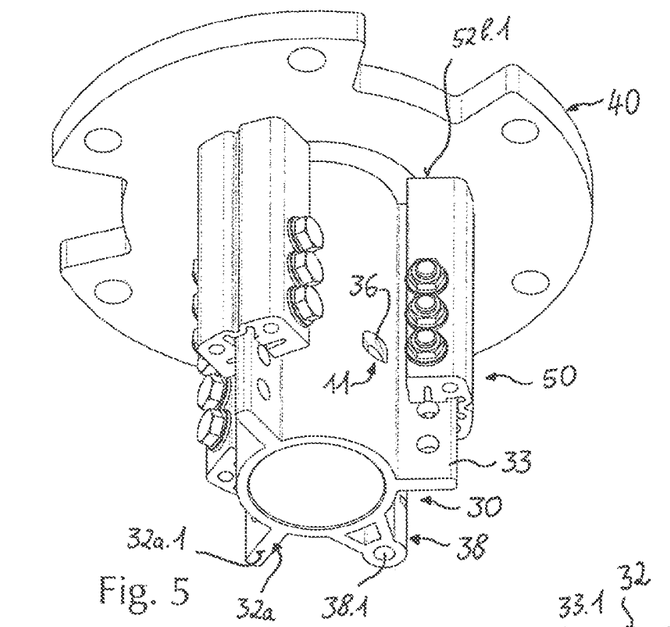
In FIG. 5 in a perspective side view individual components of the mounting device shown in FIG. 1.

In FIG. 4 a plane lower front face 42*a*.1 of the flange plate 40 is shown, onto which the respective support 50 may abut on a planar upper front face 52.*b*.1 (indicated in FIG. 5). The respective support 50 comprises fastening means 51 passing through, in particular internally threaded bores, with which screws, for example, may engage. The respective fastening portion 33 abuts on opposite jaws 53. The jaws may be pressed by means of the screws 80 against a respective radial flank 33.1. Each jaw 53 includes single jaw portions 53*a*, 53*b*, which are adapted to ensure a secure or stressable connection of the respective support 50 with the mounting apparatus 30. In addition, the respective support 50 includes a corrugation 54 that constitutes a face pointing outwards at least section-wise, and due to that the support 50 may be bent in a comparatively simple and flexible way and be mounted to the respective fastening portion 33. The opposite jaws 53 define a radial cavity 55, in particular in a slot shape, that is formed to correspond geometrically to the respective fastening portion 33. Here the fastening portions 33 extend in a radial direction outwards from a cylindrical outer lateral surface 31 and extend said outer lateral surface. The mounting apparatus 30 comprises an at least section-wise cylindrical inner lateral surface 37 that defines the cavity K or surrounds it radially.

FIG. 5 shows the mounting apparatus 30 in a state mounted to a flange plate 40 from a lower side. The retainer 38 for a rotational lock and also the individual fastening portions 33 define a lower front face 32*a*, which is formed by a planar lower front face 32*a*.1. On this front face 32*a*.1 the adjustment apparatus may abut. The mounting apparatus 30 may be adapted as a continuous cast profile, for example. On the lateral surface of the mounting apparatus 30 one or more passages 36 are provided, in particular in a tangential direction, which constitute a part of the axial lock 11.

Figure 6:
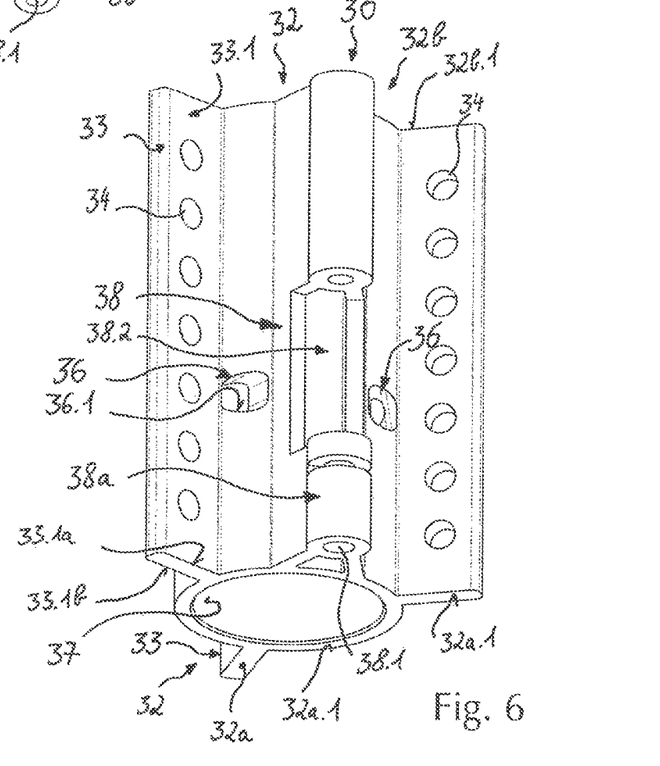
In FIG. 6 in a perspective side view a mounting apparatus of the mounting device shown in FIG. 1.

In FIG. 6 the mounting apparatus 30 is shown separately. The mounting apparatus 30 is formed as cast profile and includes opposite front faces 32. Similar to the lower front face 32*a* an upper front face 32*b* is formed by a planar upper front face 32*b*.1. Along each of the fastening portions 33 a plurality of openings or fastening means 34 are provided, as for example threaded bores or bores. The passages 36 define a support surface 36.1, respectively, on which the securing element 70, shown in FIG. 2, may abut. The supporting surface 36.1 may also be formed at least partly by a chamfer, edge or milled recess 37.1 (see FIG. 2) formed on the inner lateral surface 37. A force flux path of a weight to be transferred passes through said support surfaces 36.1. The passages 36 adjoin radially inwards to at least two of the fastening portions 33. Each fastening portion 33 comprises opposite radial flanks 33.1*a*, 33.1*b*, in particular aligned parallel to each other. The rotational lock 38 or the retainer is formed as a locking tube portion. The rotational lock 38 includes a lower tube-like retainer portion 38*a*. The lower retainer portion 38*a* may be partitioned, in particular by a slot, wherein additional securing of a/the rotational lock element may be enabled by means of a spring connector. The retainer 38 includes an access 38.2 adapted as cutout. On said access or in the region of said access a bolt may be plugged in the through bore 38.1 on the lower retainer portion 38.*a*, that is from above in the adjustment apparatus that is arranged on the lower front face 32*a*.1.

Figure 7:
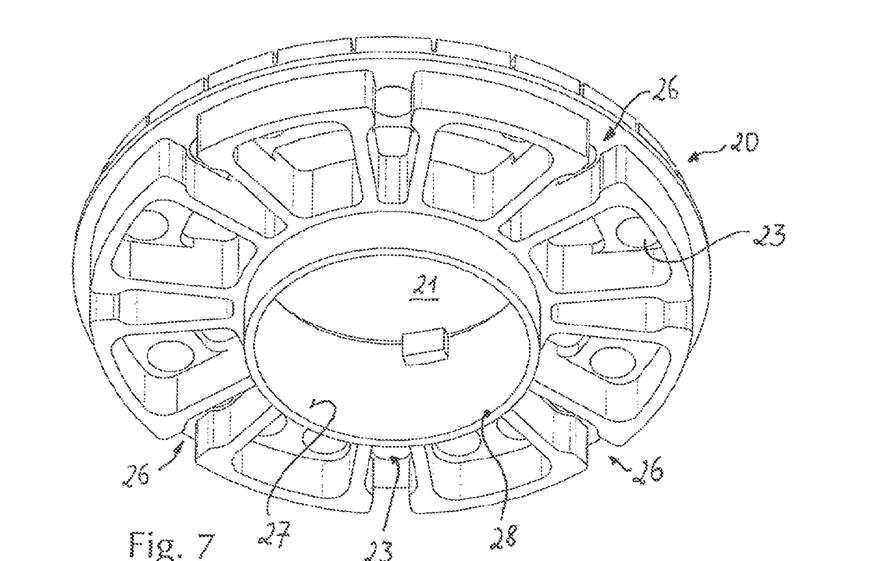
In FIG. 7 in a perspective view from below the adjustment apparatus shown in FIG. 1.
Figure 8:
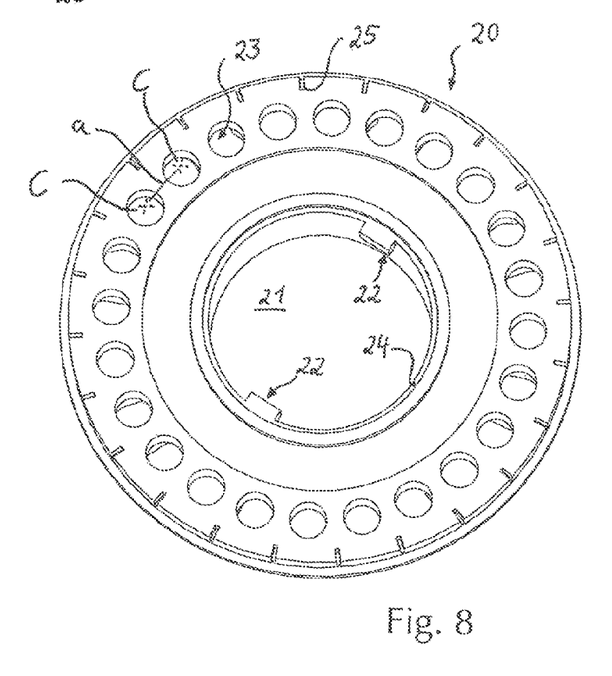
In FIG. 8 in a perspective view from above the adjustment apparatus shown in FIG. 7.

In FIG. 7 the mounting apparatus 20 is shown from below. The adjustment apparatus 20 may also be denoted as a flat ring. The spindle (not shown) may be passed through a passage 21. A rotational lock 22 (optionally also acting as centering) is arranged on an inner lateral surface 27, in particular adapted as a spring, that is formed to correspond geometrically to a respective groove of the spindle. Preferably two springs 22 are provided, as shown in FIG. 8. The springs 22 are arranged at an upper rim of the adjustment apparatus 20. On the lower side the adjustment apparatus 20 comprises a protruding rim 28 that facilitates an exact alignment or centering relative to the spindle due to a comparatively large axial extension. On the lower side of the adjustment apparatus 20 recesses 26 or radial slots are provided which a technician may access by using a tool (for example a screwdriver), in particular radially from outside, to rotate the adjustment apparatus 20 and thus the spindle. This way the relative rotational position may be adjusted, in particular without disassembly of any cover or enclosure. As already described regarding FIG. 1, the adjustment apparatus includes a plurality of coupling points 23 which are formed in a geometrically corresponding way to a rotational locking means, in particular a bolt. The coupling points 23 are arranged on the pitch circle, in particular concentrically about a center of the adjustment apparatus 20. According to a variant, the coupling points 23 are formed as openings and with at least approximately the same diameter as the through bore 38.1 shown in FIG. 6.

In FIG. 8 the adjustment apparatus 20 is shown from above. The adjustment apparatus 20 comprises an annular support surface 24 which may also be formed at least partly by the springs 22. The support surface 24 is formed in a geometrically corresponding way to a radial protruding rim 4.4 (FIG. 9) of the spindle. In addition, on an outer periphery of the adjustment apparatus 20 fastening means for a cover or enclosure are provided. The fasting means are provided as slots 25 extending in a radial direction. Said configuration facilitates plugging in from above or from the side in a radial direction. As shown, the adjustment apparatus 20 is formed as a flat ring and comprises an at least 12-point rotational symmetric design regarding the arrangement of the coupling points or openings, and an exactly 24-point rotational symmetric design in the exemplary embodiment shown. That is, the adjacent couplings points 23 or openings are arranged at a maximum angular distance a of 30° from one another related to the center thereof in an at least 12-point rotational symmetric design, and adjacent coupling points or openings are arranged in an angular distance a of 15° from one another related to the center thereof for the 24-point rotational symmetric design shown.

Figure 9:
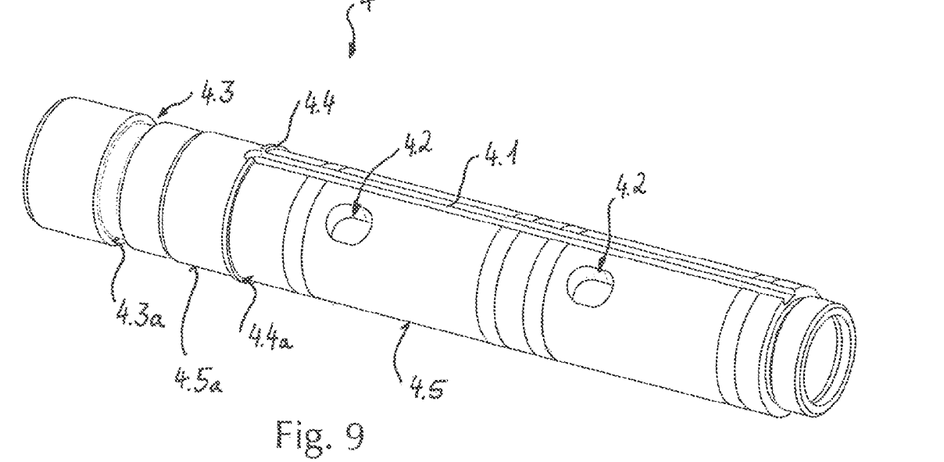
In FIG. 9 in perspective view the spindle shown in FIG. 3.

In FIG. 9 the mounting apparatus 4 is shown in detail. The spindle 4 comprises two axial grooves 4.1 that are arranged opposite to one another in the axial direction. The respective axial groove extends to a step or radially protruding rim 4.4, thus the springs may be pushed in the grooves 4.1 up to the rim 4.4. In addition, the spindle includes two recesses 4.2, that are arranged at an distance axially to one another and pass through an outer lateral surface 4.5. A cable, in particular a slip-ring cable, may be fed through the recesses 4.2, respectively. Above the rim 4.4 a centering surface portion 4.5 a is provided by means of which the spindle 4 may be centered in the cavity K. The rim 4.4 defines an annular support surface 4.4*a* onto which the adjustment apparatus may abut. The peripheral groove 4.3 defines an annular support surface 4.3*a* by means of which the weight of the stand device may be transferred from the spindle 4 to an axial lock 11 (not shown).

Figure 10:
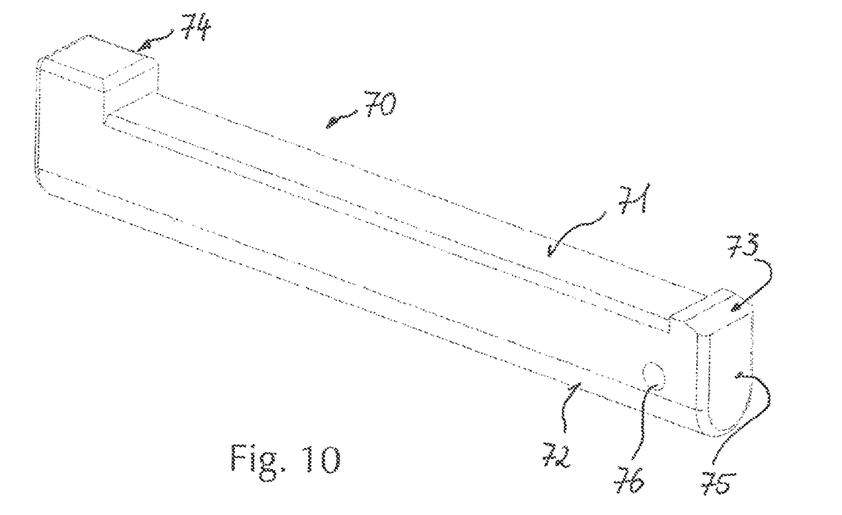
In FIG. 10 in a perspective view a securing element of the mounting device shown in FIG. 1.

In FIG. 10 the securing element 70 adapted as a latch is shown in detail. The latch 70 includes a top support surface 71 onto which the support surface 4.3*a* shown in FIG. 9 may abut. Further, the latch 70 includes a lower contact surface 72 that is curved in the present example, by means of which the latch 70 is supportable in the passage 36 on the mounting apparatus 30. The contact surface 72 is curved with a predefined curvature radius, whereby a minor notch effect may be ensured. The curved contact surface 72 may ensure a small surface pressure. The latch 70 has an U-shaped cross-section area 75 which basically has the same geometry along the whole length of the latch 70. A respective free end of the latch 70 includes steps 73, 74 that allows to secure the latch 70 in the passage 36. One of the steps is smaller than the other.

The step 73 is adapted as mounting chamfer and may prevent a slipping out of the latch 70. The step 74 also prevents a slipping out. The step 74 is preferably formed in a height at which the latch 70 may not be pushed through the corresponding passage, but is blocked by step 74.

In the region of one of the both free ends, the latch includes a through bore 76 onto which the latch 70 may be secured, in particular by means of a spring connector.

Figure 11:
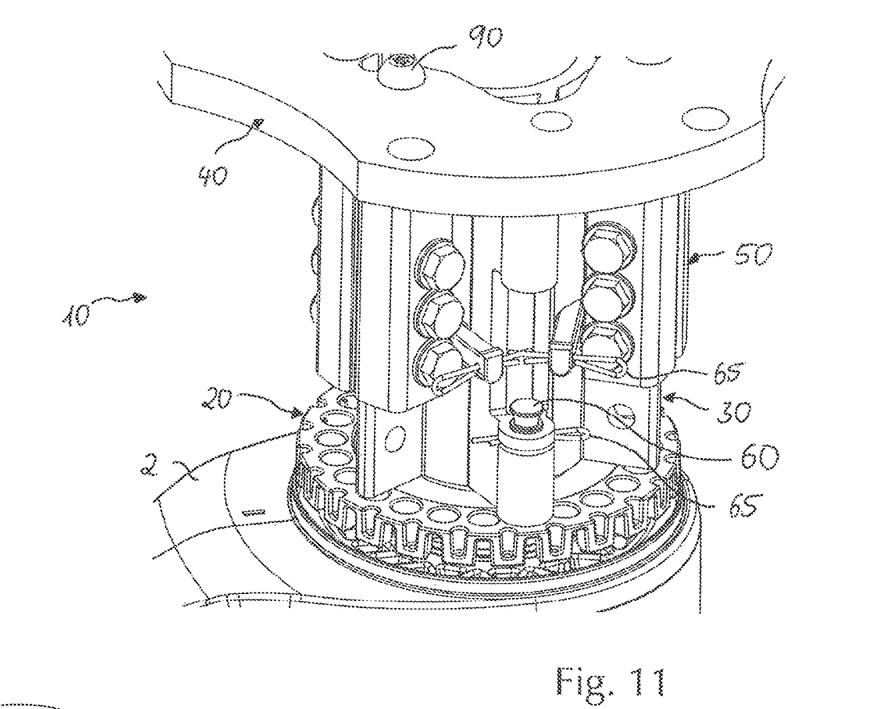
In FIG. 11 in a perspective view a mounting device according to a further exemplary embodiment of the invention in an arrangement mounted to a stand device including mounted securing elements.

FIG. 11 shows a mounting device 10 wherein a rotational lock element 60 is secured on the mounting apparatus 30 by using a spring connector 65 in an engagement position with the adjustment apparatus 20.

Figure 12:
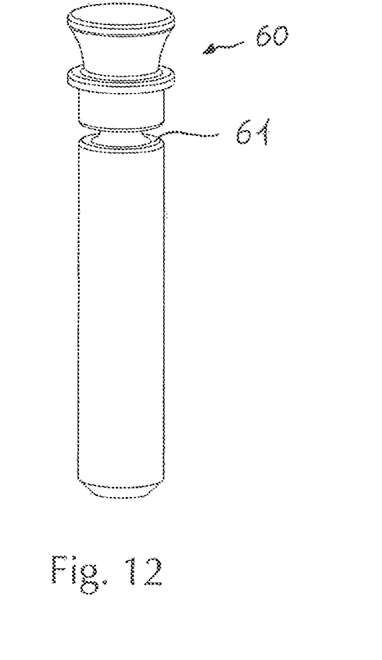
In FIG. 12 in a perspective view a rotational lock element configured to secure a rotational position.

As can be seen in FIG. 12, the spring connector 65 engages with the groove 61 of the bolt or the rotational lock element 60. The two latches 70 are also secured by corresponding spring connectors 65, wherein each spring connector engage with the corresponding through bore of the respective latch 70.

Figure 13:
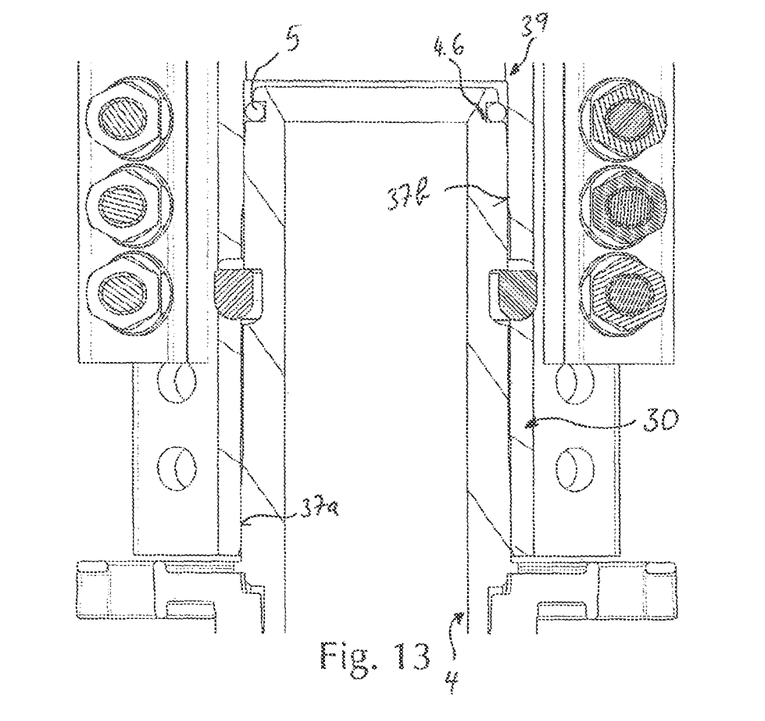
In FIG. 13 in a side section view a further exemplary embodiment of a mounting device; and In FIG. 14 a spindle adapted for the mounting device shown in FIG. 13.
Figure 14:
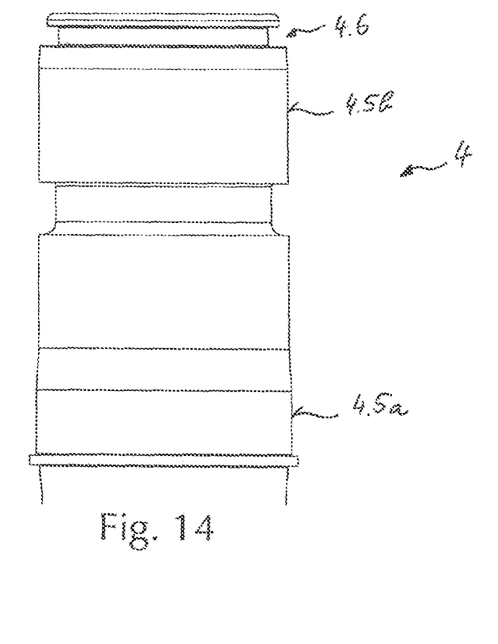

FIGS. 13 and 14 show how a simplified assembly may be realized by using two mating faces 37*a*, 37*b* and corresponding surface portions 4.5*a*, 4.5*b* of the spindle. The spindle 4 includes a step 4.6 where an O-ring 5 is arranged. Hereto, a corresponding step 39 is formed on the mounting apparatus 30. The second mating face 37*b* has an inner diameter that is smaller than that of the first mating face 37*a*. Thus, a spindle 4 may be mounted without the risk of jamming on the one side, and, on the other side, mounting may be performed in a very robust way on surface portions 4.5*a*, 4.5*b* that are spaced far apart from one another.

LIST OF REFERENCE NUMBERS

1 Stand device—in particular a ceiling stand device
2 (First) carrier or carrier arm
3 (Second) carrier or carrier arm
4 Connection component, in particular a spindle
4.1 Rotational lock, in particular a groove in the connection component, preferably an axial groove arranged in the longitudinal direction
4.2 Recess
4.3 Peripheral groove
4.3*a* Annular support surface
4.4 Step or radially protruding rim
4.4*a* Annular support surface
4.5 Outer lateral surface
4.5*a* Centering surface portion or first mating face
4.5*b* Second mating face
4.6 Groove for an O-ring on the free end of the spindle
5 O-ring
10 Mounting device
10*a* Adaptable mechanism, in particular, an adjustable rotational coupling
11 Axial lock
20 Adjustment apparatus, in particular flat ring
21 Passage
22 Rotational lock, in particular a spring
23 Coupling point for a respective rotational position, in particular an opening or a bore
24 Annular supporting surface
25 Fastening means for cover, in particular an upper side slot
26 Recess, in particular on the lower side, that is accessible radially from outside
27 Inner lateral surface
28 Rim or centering
30 Mounting apparatus, in particular a basic body configured as a ceiling tube, preferably adapted as a continuous cast profile
31 Outer lateral surface
32 Front face
32*a* Lower front face
32*a*.1 Planar lower front face
32*b* Upper front face
32*b*.1 Planar upper front face
33 Fastening portion, in particular, crosspiece
33.1 Radial flank at the fastening portion
33.1*a*, 33.1*b* Opposite radial flanks, in particular arranged parallel to one another
34 Fastening means, in particular bore or threaded bore
36 Passage, in particular in a tangential or a radial direction
36.1 Supporting surface
37 Inner lateral surface, in particular, at least section-wise cylindrical
37*a* First mating face
37*b* Second mating face
37.1 Chamfer, edge or milled recess
38 Retainer for rotational lock element, in particular a locking tube
38*a* Lower retainer portion, in particular tube-like
38.1 Through bore, in particular in an axial direction
38.2 Access, in particular cutout
38.3 Upper access region (interface)
39 Step
40 Flange plate
41 Opening, in particular a bore
42*a*.1 Planar lower front face
42 Radial groove
50 Support, in particular opening, preferably adapted as continuous cast profile
51 Fastening means, in particular an opening, preferably internally threaded bore
52*b*.1 Planar upper front face
53*a*, 523*b* Opposite jaw portions of a jaw
54 Corrugation
55 Radial cavity
60 Rotational lock element, in particular a bolt
61 Groove 65 Spring connector
70 Securing element for axial lock, in particular a latch
71 Upper side supporting surface
72 Lower side contact surface
73 Step at a free end
74 Step at a free end
75 Cross-sectional area
76 Through bore
80 Fastening element at support, in particular a screw
90 Fastening element at flange plate, in particular a screw
a Angular distance
C Center
D Axis of rotation
G Weight
K Cavity
X Radial direction or horizontal direction
Y Transverse direction
Z Longitudinal direction or axial direction or vertical direction The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A mounting device for a stand device for arrangement in an operating room to position or displace a medical device in an operating room, in particular by a rotational motion, comprising:
   a mounting apparatus which extends along an axis of rotation in a longitudinal direction with a cavity for accommodating a rotatably supportable connection component of the stand device, wherein the mounting apparatus comprises a tube-like retainer for a rotational lock element, wherein the retainer comprises an access radially from outside, and wherein the access includes an upper access region onto which a rotational lock element may abut in a predefined axial position; and
   an adjustment apparatus for arranging the connection component in a position, which can be predefined, in relation to the mounting apparatus;
   wherein the mounting device forms a rotational coupling that is adjustable around the axis of rotation for supporting the connection component on the mounting apparatus.

2. The mounting device according to claim 1, wherein the adjustable rotational coupling is formed by the adjustment apparatus and the mounting apparatus, wherein the adjustment apparatus can be positioned in a predefined rotational position around the axis of rotation in relation to the mounting apparatus and is supportable in a rotationally fixed manner.

3. The mounting device according to claim 1, wherein the adjustment apparatus comprises a rotational stop, in particular a groove or spring, that is formed to correspond geometrically to a rotational stop, in particular a groove or spring, arranged on the connection component.

4. The mounting device according to claim 1, wherein the adjustment apparatus comprises a plurality of coupling points, in particular openings or passages, for defining a rotational position of the rotational coupling, respectively, which are preferably arranged on a pitch circle, wherein the adjustment apparatus is preferably annularly, in particular is adapted as an annular disk.

5. A mounting device for a stand device for arrangement in an operating room to position or displace a medical device in an operating room, in particular by a rotational motion, comprising:
   a mounting apparatus which extends along an axis of rotation in a longitudinal direction with a cavity for accommodating a rotatably supportable connection component of the stand device;
   an adjustment apparatus for arranging the connection component in a position, which can be predefined, in relation to the mounting apparatus; and
   an axial lock, by means of which the connection component is supportable in a predefined axial position on the mounting apparatus, in particular rotatable in relation to the mounting apparatus, wherein the mounting apparatus is adapted to mount and rotatably support the connection component in a predetermined relative axial position, wherein a chamfer, edge or milled recess is preferably provided on an inner lateral surface surrounding the cavity;
   wherein the mounting device forms a rotational coupling that is adjustable around the axis of rotation for supporting the connection component on the mounting apparatus.

6. The mounting device according to claim 5, wherein the axial lock comprises a passage arranged tangentially to the mounting apparatus, which passes through an outer lateral surface of the mounting apparatus, preferably at two points, and which intersects an/the inner lateral surface of the mounting device, wherein a support surface is preferably formed on the passage that is configured to transfer a force applied from the connection component to the mounting apparatus.

7. The mounting device according to claim 5, wherein the axial lock comprises at least one securing element, in particular a latch or bolt, which is adapted and configured to transfer the weight of the stand device from the connection component to the mounting apparatus, wherein the securing element is preferably arrangeable tangentially to the mounting apparatus and is formed to correspond geometrically to the passage, in particular on a lower side contact surface.

8. The mounting device according to claim 1, wherein the mounting device comprises two mating faces in different sizes that are formed to correspond to mating faces of the connection component.

9. A mounting device for a stand device for arrangement in an operating room to position or displace a medical device in an operating room, in particular by a rotational motion, comprising:
   a mounting apparatus which extends along an axis of rotation in a longitudinal direction with a cavity for accommodating a rotatably supportable connection component of the stand device;
   an adjustment apparatus for arranging the connection component in a position, which can be predefined, in relation to the mounting apparatus; and a plurality of openings in the adjustment apparatus to define a rotational position, respectively, which are arranged on a pitch circle, wherein the adjustment apparatus is annular, wherein the mounting apparatus comprises a tube-like retainer for a rotational lock element, wherein the retainer is arranged on an outer lateral surface of the mounting apparatus, wherein the retainer comprises an access radially from outside with an upper access region onto which the rotational lock element can abut, wherein the adjustment apparatus comprises a groove or spring that is formed to correspond geometrically to a rotational stop arranged on the connection component, wherein the mounting device comprises an axial lock that includes a chamfer, edge or milled recess provided on an inner lateral surface of the mounting apparatus surrounding the cavity, wherein the axial lock comprises a passage tangentially arranged on the mounting apparatus that passes through an outer lateral surface of the mounting apparatus and intersects the inner lateral surface;

wherein the mounting device forms a rotational coupling that is adjustable around the axis of rotation for supporting the connection component on the mounting.

10. The mounting device according to claim 1, wherein the adjustment apparatus is formed as a flat ring and comprises an at least 12-point rotational symmetric design regarding the arrangement of the coupling points, in particular an at least 24-point rotational symmetric design.

11. A mounting system including a mounting device according to claim 1, wherein the mounting system comprises a connection component adapted as a spindle and a rotational lock element, and at least one securing element for an axial lock, wherein a rotational stop is formed on the spindle to correspond geometrically to a rotational lock formed on the adjustment apparatus.

12. Use of an mounting system according to claim 11 on a stand device arranged in the operating room, respectively, to position or displace a medical device, in particular by a rotational movement, wherein the adjustment apparatus or the mounting apparatus define an adjustable rotational position of a connection component of the stand device in relation to a flange plate by means of which the stand device is fastened in the operating room.

13. The mounting device of claim 1 wherein the retainer is arranged on an outer lateral surface of the mounting apparatus or constitutes the outer lateral surface at least in sections.

14. The mounting device of claim 1 wherein the access is adapted as a cutout.

15. The mounting device of claim 1 wherein the cavity is substantially cylindrical and oriented in the longitudinal direction.

16. The mounting device of claim 1 wherein the connection component is a spindle.

17. The mounting device of claim 1 wherein the retainer is arranged on an outer lateral surface of the mounting apparatus or constitutes the outer lateral surface at least in sections; the access is adapted as a cutout; the cavity is substantially cylindrical and oriented in the longitudinal direction; and the connection component is a spindle.

18. The mounting device of claim 5 wherein the retainer is arranged on an outer lateral surface of the mounting apparatus or constitutes the outer lateral surface at least in sections; the access is adapted as a cutout/the cavity is substantially cylindrical and oriented in the longitudinal direction; and the connection component is a spindle.

19. The mounting device of claim 9 wherein the retainer is arranged on an outer lateral surface of the mounting apparatus or constitutes the outer lateral surface at least in sections; the access is adapted as a cutout; the cavity is substantially cylindrical and oriented in the longitudinal direction; and the connection component is a spindle.

* * * * *